United States Patent [19]

Matsuno et al.

[11] Patent Number: 5,576,295
[45] Date of Patent: Nov. 19, 1996

[54] AGENT FOR SUPPRESSING THE MOTOR ACTIVITY OF GASTROINTESTINAL TRACTS

[75] Inventors: Seiki Matsuno; Iwao Sasaki; Akira Ohneda, all of Sendai; Kazuyuki Sasaki, Ohimachi, all of Japan

[73] Assignee: Nisshin Flour Milling Co., Ltd., Tokyo, Japan

[21] Appl. No.: 324,502

[22] Filed: Oct. 18, 1994

[30] Foreign Application Priority Data

Oct. 18, 1993 [JP] Japan .................................. 5-259798

[51] Int. Cl.$^6$ ............................ A61K 38/04; A61K 49/00
[52] U.S. Cl. ................................................ 514/12; 514/21
[58] Field of Search .............................. 530/324; 514/12, 514/21

[56] References Cited

FOREIGN PATENT DOCUMENTS

| | | |
|---|---|---|
| 0586812 | 3/1994 | European Pat. Off. . |
| 0612531 | 8/1994 | European Pat. Off. . |
| 4-364199 | 12/1992 | Japan . |

OTHER PUBLICATIONS

B. Ahrén and I. Lundquist, "Effects of Glicentin on Insulin Secretion", Horm. Metal Res. 12, pp. 582–586, (1980).
F. Sundby, et al., "Purification and Characterization of a Protein from Porcine Gut with Glucagon–Like Immunoreactivity", *J. Horm. Metab. Res.*, vol. 8, 1976, pp. 366–371.
Lars Thim, et al., "The Primary Structure of Porcine Glicentin (Prolucagon)", *Regulatory Peptides*, vol. 2, 1981, pp. 139–150.
Graeme I. Bell, et al., "Exon Duplication and Divergence in the Human Preproglucagon Gene", *Nature*, vol. 304, Jul. 1983, pp. 368–371.

*Primary Examiner*—Howard E. Schain
*Assistant Examiner*—Lynn P. Touzeau
*Attorney, Agent, or Firm*—Oblon, Spivak, McClelland, Maier & Neustadt, P.C.

[57] ABSTRACT

Agents for suppressing the motor activity of gastrointestinal tracts, which comprise glicentin as an active ingredient. They can be used as an adjunct for use in examination of gastrointestinal tracts by radiography or endoscopy.

6 Claims, 1 Drawing Sheet

AGENT FOR SUPPRESSING THE MOTOR ACTIVITY OF GASTROINTESTINAL TRACTS

FIELD OF THE INVENTION

This invention relates to an agent for suppressing the motor activity of gastrointestinal tracts, which comprises glicentin as an active ingredient. More particularly, the invention relates to the agent which is suitable for temporarily suppressing the motor activity of gastrointestinal tracts during the abdominal examination.

BACKGROUND OF THE INVENTION

Glicentin which is one of enteroglucagons is a peptide comprising 69 amino acid residues. For example, human glicentin is composed of the following amino acid sequence (SEQ ID NO: 1)

Arg-Ser-Leu-Gln-Asp-Thr-Glu-Glu-Lys-Ser-Arg-Ser-Phe-Ser-Ala-Ser-Gln-Ala-Asp-Pro-Leu-Ser-Asp-Pro-Asp-Gln-Met-Asn-Glu-Asp-Lys-Arg-His-Ser-Gln-Gly-Thr-Phe-Thr-Ser-Asp-Tyr-Scr-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala

Glicentin was isolated and purified from porcine intestine by F. Sundby et al in 1976 (F. Sundby et al, Horm. Metab. Res. 8 (1976) 366–371). The structure of glicentin has been established by A. J. Moody et al (L. Thim and A. J. Moody, Regul. Pept. 2 (1981) 139–150).

It has been difficult to study human glicentin using its purified product, since the human organs such as gastrointestinal tracts were difficult to obtain in large quantities.

Now, the present inventors were successful in synthesizing DNA corresponding to the amino acid sequence of human glicentin which was deduced by G. I. Bell (Nature, 304, 368–371 (1983)) from the sequence of human preproglucagon gene and preparing human glicentin by means of genetic engineering procedure using the synthesized DNA which was disclosed in Japanese Patent Kokai Hei 4-364199. This results in easy availability of human glicentin as its purified product in large amounts.

Butylscopolamine bromide injections have been used as the agents for temporarily suppressing the motor activity of gastrointestinal tracts in the medical examinations of the digestive tracts, such as gastrointestinal roentgenologic examination and endoscopic examination. However, such butylscopolamine bromides have the effect on the systemic autonomic nervous system, thus leading to the disadvantages of bringing about side effects such as thirst, dizziness and ataxia. Further, there is glucagon as peptidic agents for suppressing the motor activity of gastrointestinal tracts. However, such glucagon is not a suitable agent, because of its unfavorable action to induce a sudden rise in blood glucose.

SUMMARY OF THE INVENTION

The present inventors found for the first time that human glicentin suppresses the gastrointestinal motility, thus leading to the present invention.

According to the present invention, there is provided an agent for suppressing the motor activity of gastrointestinal tracts, which comprises glicentin as an active ingredient.

The present invention also provides a method for temporarily suppressing the motor activity of gastrointestinal tracts, which comprises administering an effective amount of glicentin to a subject for the medical examination.

DETAILED DESCRIPTION OF THE INVENTION

Figure 1:
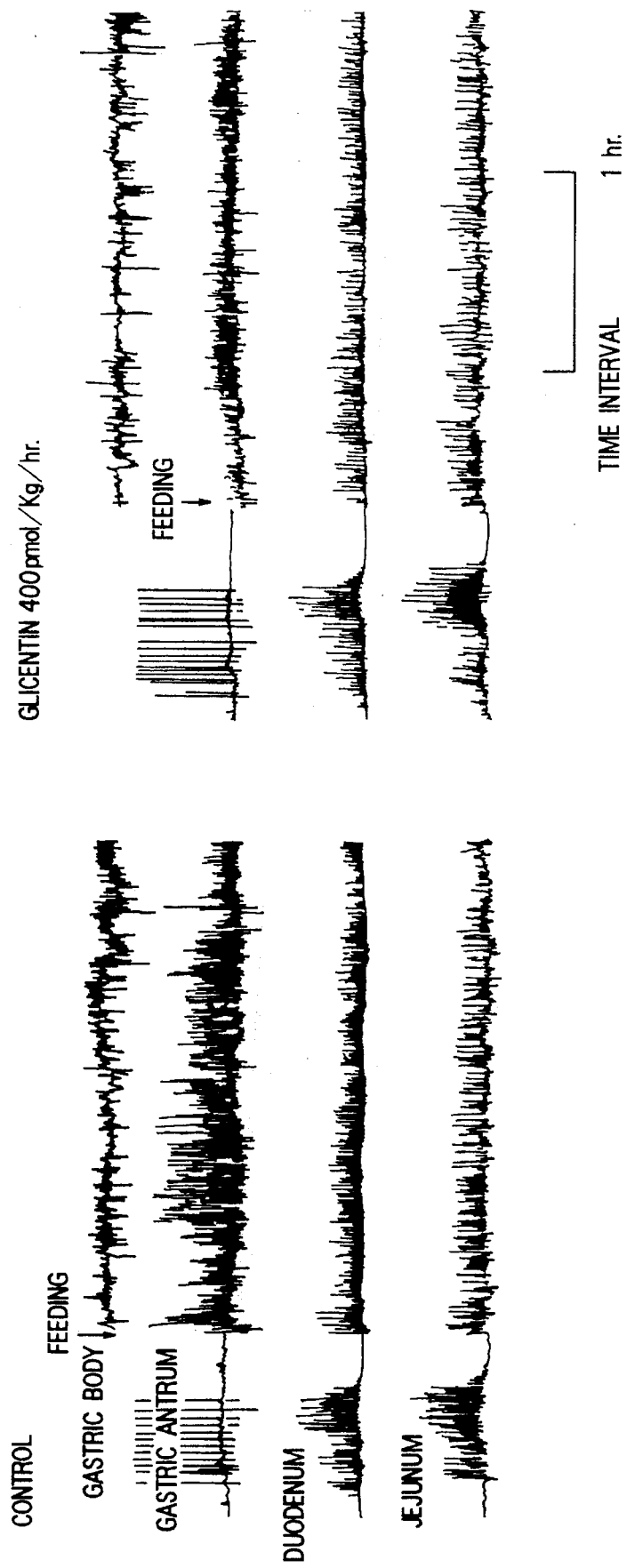
FIG. 1 is a figure showing the effect of glicentin on the motor activity of gastrointestinal tracts in the post-feed period in comparison with a control.

In the present invention, an administration of glicentin suppresses the gastrointestinal motility which enables one to use it as an adjunct for use in the medical examinations of the digestive tracts such as gastrointestinal roentgenologic examination, abdominal MRI examination and endoscopic examination.

Further, glicentin can be used in the treatment of reduction in function of gastrointestinal tracts after operation, for example, in damping syndrome as well as in the treatment of duodenal ulcer in conjection with the inhibition of peristalsis of the stomach and rapid migration of food from the stomach to the jejunum.

The term "agent for suppressing the motor activity of gastrointestinal tracts" as used herein includes an adjunct for temporarily suppressing the motor activity of gastrointestinal tracts by administration of glicentin to a subject for the medical examination and also a therapeutic agent for the treatment of the disease caused by the resection and shunt of the small intestine such as short gut syndrome, cul-de-sac syndrome and indigestible malabsorption syndrome such as the disease caused by resection of the stomach, e.g., dumping syndrome.

The term "adjunct" as used herein refers to an agent for use in examination of gastrointestinal tracts, e.g., by radiography or endoscopy.

The term "gastrointestinal tracer" as used herein includes the stomach and intestine including the tubular portion between the stomach and the anus.

Glicentin which can be used in the present invention includes any glicentin of an animal origin such as human, porcine, bovine, hamster, rat and guinea pig, as well as glicentin containing additional methionine (Met) at the N-terminus, which are prepared by a genetic engineering procedure or a synthetic process. Preferably, human glicentin is used in view of an undesirable allergic reaction or the like produced when being administered to humans. More preferably, there is used human glicentin (natural type) not containing additional methionine (Met) at the N-terminus.

Human glicentin (natural type) has the following amino acid sequence (SEQ ID NO: 1):

Arg-Ser-Leu-Gln-Asp-Thr-Glu-Glu-Lys-Ser-Arg-Ser-Phe-Ser-Ala-Ser-Gln-Ala-Asp-Pro-Leu-Ser-Asp-Pro-Asp-Gln-Met-Asn-Glu-Asp-Lys-Arg-His-Ser-Gln-Gly-Thr-Phe-Thr-Ser-Asp-Tyr-Scr-Lys-Tyr-Leu-Asp-Ser-Arg-Arg-Ala-Gln-Asp-Phe-Val-Gln-Trp-Leu-Met-Asn-Thr-Lys-Arg-Ash-Arg-Asn-Asn-Ile-Ala

Further, human glicentin containing additional methionine (Met) at the N-terminus has the following amino acid sequence (SEQ ID NO: 2):

Met-Arg-Ser-Leu-Gln-Asp-Thr-Glu-Glu-Lys-Ser-Arg-Ser-Phe-Ser-Ala-Ser-Gln-Ala-Asp-Pro-Leu-Ser-Asp-Pro-Asp-Gln-Met-Asn-Glu-Asp-Lys-Arg-His-Set-Gin-Gly-Thr-

Phe-Thr-Ser-Asp-Tyr-Ser-Lys-Tyr-Leu-Asp-Ser-Arg-Arg-
Ala-Gln-Asp-Phe-Val-Gln-Trp-Leu-Met-Asn-Thr-Lys-Arg-
Asn-Arg-Asn-Asn-Ile-Ala

The above human glicentin can be prepared by a genetic engineering procedure or a synthetic process from a gene of the DNA sequence corresponding to the above amino acid sequence. An example of the genetic engineering procedure is a process of producing a desired human glicentin which comprises preparing a synthetic gene encoding human glicentin amino acid sequence of the following DNA sequence (SEQ ID NO: 3) which has been suggested by the present inventors in Japanese Patent Koka. Hei 4-364199, introducing the synthetic gene into plasmid, transforming *E. coli* with the resultant plasmid and culturing the transformant.

mg, advantageously 0.1 to 1 mg per 5 ml and the tablets capsules or granules may contain glicentin in an amount of 0.01 to 10 mg, advantageously 0.1 to 1 mg.

From the chemical structure, glicentin is considered to undergo a denaturation by an acid within intestine, a decomposition by digestion and a reduction in activity by such denaturation, when administered orally to human body. Therefore, it is recommendable to release the active ingredient, glicentin within intestine using an enteric coating. Thus the active ingredient is preferably coated with a conventional enteric coating agent in the oral administration. The enteric coating agents include synthetic polymers such as EUDRAGIT®, polyacrylate base (available from Rohm

| 5'<br>3' | CGTTCC<br>GCAAGG | CTGCAGGACA<br>GACGTCCTGT | CTGAAGAAAA<br>GACTTCTTTT | ATCTCGTTCT<br>TAGAGCAAGA | TTCTCTGCTT<br>AAGAGACGAA | CTCAGGCTGA<br>GAGTCCGACT |
|---|---|---|---|---|---|---|
| | CCCACTGTCG<br>GGGTGACAGC | GATCCAGACC<br>CTAGGTCTGG | AGATGAACGA<br>TCTACTTGAT | AGACAAACGT<br>TCTGTTTGCA | CATTCTCAGG<br>GTAAGAGTCC | GTACTTTCAC<br>CATGAAAGTG |
| | TTCTGACTAC<br>AAGACTGATG | TCTAAATACC<br>AGATTTATGG | TGGACTCTCG<br>ACCTGAGAGC | TCGAGCTCAG<br>AGCTCGAGTC | GACTTCGTTC<br>CTGAAGCAAG | AGTGGCTGAT<br>CTACCGACTA |
| | GAACACTAAA<br>CTTGTGATTT | CGTAACCGTA<br>GCATTGGCAT | ACAACATCGC<br>TGTTGTAGCG | C 3'<br>G 5' | | |

Other processes of producing the human glicentin include introducing into plasmid a gene of another DNA sequence corresponding to the above amino acid sequence of glicentin, transforming *E. coli, Bacillus subtilis,* yeast or other microorganism with the resultant plasmid and culturing the transformant or a alternatively culturing a human glicentin productive cell. However, it should be understood that human glicentin used in the invention is not limited to one produced by the specific process and any human glicentin can be employed in the invention so far as it has the above amino acid sequence.

Usually, glicentin as the active ingredient can be administered orally or parenterally in the form of suitable pharmaceutical preparations. Such pharmaceutical preparations can be formulated in a conventional manner using one or more pharmaceutically acceptable vehicles, adjuvants and additives, e.g., binders, diluents, solubilizers, stabilizers, buffers, lubricants, coating agents, antioxidants, sweeteners, flavors, colorants and the like. Suitable preparations include powders, granules, tablets, capsules, injections, syrups, suspensions, emulsions or the like. If necessary, the active ingredient may be administered in combination with other drugs such as antacid, muscarine receptor antagonist and prostaglandin. It may be in bilayered or multilayered tablet with other drugs. The tablets may also be coated with a conventional coating to form, e.g., sugar-coated, enteric-coated or film-coated tablets.

In the formulation of solid preparations such as tablets and capsules there may be used suitable additives such as lactose, refined sugar, crystalline cellulose, corn starch, calcium phosphate, sorbitol, carboxymethylcellulose, gum arabic, polyvinylpyrrolidone, hydroxypropylcellulose, glycerin, polyethylene glycol, stearic acid, magnesium stearate and talc. In the formulation of liquid preparations such as injections and syrups, suitable additives may be used such as sodium chloride, sorbitol, glycerin, olive oil, propylene glycol and ethyl alcohol.

For a preferred unit dosage form for oral administration, for instance, the aqueous or oily solutions, suspensions or emulsions may contain glicentin in an amount of 0.01 to 10

Pharma), semisynthetic polymers such as cellulose acetate phthalate or the like.

A preferable administration of glicentin is parenteral for the reason of its not undergoing denaturation or decomposition. The parenteral administration includes subcutaneous, intravenous, intramuscular and intraperitoneal injections. Glicentin can be formulated into the aqueous or oily solutions, suspensions or emulsions. Preferably, glicentin is administered in the form of depot preparations for a prolonged effect of glicentin over a long period of time.

A dose of the active ingredient can be varied depending on the route of administration, the symptoms, age, sex and weight of patients or the subject for medical examination and other factors, but suitably can be in the range so as to provide a level of 100 pM to 10,000 pM in blood. Usual parenteral dosage for adult human ranges from 0.5 µg/kg to 500 µg/kg. However, lower or higher amount may be administered within the safety range.

When 10 mg/kg of human glicentin (natural type) is intraperitoneally administered to male BALB/c mice (6 weeks age), no change in appearance is observed.

The present invention is further illustrated by the following example. The numerical values in the tables are shown by average value±standard error.

EXAMPLE 1

An experiment was performed as described below in order to examine the action of glicentin on a motility of gastrointestinal tracts.

Six hybrid dogs weighing 16–18 kg were sutured with strain gauge transducers (manufactured by Star Medical, F121S) at a site of the gastric antrum 4 cm from the pyloric ring, a site of the duodenum for the main incurrent pancreatic duct and a site of the jejunum 10 cm from the Treitz's ligamentum, respectively, to measure the contractile force intensity of the circular muscle. Recovery period for the suture was 2 weeks.

Three of the 6 dogs were intravenously given over 1 hour 15 ml of a physiological saline solution in which 400 pmol of glicentin had been dissolved per kg of bodyweight. The remaining three received an aqueous physiological solution containing no glicentin in the same way as above as a control for comparison. The dogs were fed on 15 g of a solid diet (SD®, manufactured by Oriental Yeast K.K.) and 15 g of Vitaone® (manufactured by Nihon Pet Food K.K. and Kyodo Shiryo K.K.) per kg of bodyweight simultaneously with the intravenous administration.

Then, the motor activity of gastrointestinal tracts and length of the post-feed period were measured. The results are shown in FIG. 1 and Table 1. Intensity of the contraction in the post-feed period was integrated for the two-hour measurements and evaluated in comparison with the mean level of the signal peak in phase 3 motor activity of the gastrointestinal tracts in hunger and taken as a motor index. The results are shown in Table 2.

TABLE 1

|  | Length of post-feed period (hr.) |
| --- | --- |
| Control group | 14.8 ± 0.3 |
| Glicentin group | 13.6 ± 1.0 |

TABLE 2

|  | Motor index | |
| --- | --- | --- |
|  | Control group | Glicentin group |
| Gastric antrum | 1.670 ± 0.2 | 0.878 ± 0.1 |
| Duodenum | 1.070 ± 0.1 | 0.675 ± 0.4 |
| Jejunum | 0.829 ± 0.2 | 1.087 ± 0.2 |

The above results indicate that glicentin had no influence upon the length of the post-feed period and inhibited the post-feed motility in the vestibulum of stomach, thus demonstrating an effectiveness of glicentin as an adjunct for temporarily suppressing the motor activity of gastrointestinal tracts in the medical examination and also in the treatment of increased gastric peristalsis in damping syndrome or short gut syndrome caused by excision of the stomach or the intestinal tract.

The following examples illustrate the formulation of typical pharmaceutical preparations containing glicentin according to the invention.

PREPARATION 1

5 g of glicentin, 2 kg of lactose, 20 g of magnesium stearate and 100 g of corn starch were mixed, the mixture was compressed, the compressed mixture was pulverized to granules. The granules were formed in a tabletting machine to tablets each containing 50 μg of glicentin. The tablets were coated with cellulose acetate phthalate to form enteric-coated tablets.

PREPARATION 2

0.1 g of glicentin, 30 g of refined sugar, 26 g of 70% D-sorbitol, 0.03 g of ethyl p-oxybenzoate and 0.015 g of propyl p-oxybenzoate were dissolved in 60 g of warm water. After cooling, 0.15 g of glycerin and a solution of the flavor in 0.5 g of 96% ethanol were added. Water was added to the mixture to make up a total amount of 100 ml of syrup.

PREPARATION 3

1 g of glicentin and 99 g of lactose were mixed and the mixture was dissolved in 1 liter of distilled water for injection. The solution was filtered through a sterile filter (e.g., a 0.22 μm membrane filter), 1 ml portions of the filtered solution were dispensed into vial bottles under sterile condition and freeze dried to provide the preparations for injection. The preparations are dissolved in distilled water on use.

PREPARATION 4

5 g of glicentin, 400 g of lactose, 150 g of crystalline cellulose, 150 g of calcium stearate and 300 g of talc were mixed thoroughly, the mixture was compressed, the compressed mixture was pulverized to granules. The granules were encapsuled into two-piece capsules each containing 1.0 mg of glicentin.

What is claimed is:

1. A method for suppressing the motor activity of the gastrointestinal tract immediately prior to examination, comprising:

administering an effective amount of glicentin to a subject undergoing medical examination.

2. The method of claim 1, wherein the glicentin is human glicentin.

3. The method of claim 2, wherein the human glicentin has the following amino acid sequence (SEQ ID NO: 1):

Arg-Ser-Leu-Gln-Asp-Thr-Glu-Glu-Lys-Ser-Arg-Ser-Phe-Ser-Ala-Ser-Gln-Ala-Asp-Pro-Leu-Ser-Asp-Pro-Asp-Gln-Met-Asn-Glu-Asp-Lys-Arg-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala.

4. The method of claim 2, wherein the human glicentin has the following amino acid sequence (SEQ ID NO: 2):

Met-Arg-Ser-Leu-Gln-Asp-Thr-Glu-Glu-Lys-Ser-Arg-Ser-Phe-Ser-Ala-Ser-Gln-Ala-Asp-Pro-Leu-Ser-Asp-Pro-Asp-Gln-Met-Asn-Glu-Asp-Lys-Arg-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala.

5. The method of claim 2, wherein the human glicentin is administered at a parenteral dosage ranging from 0.5 µg/kg to 500 µg/kg.

6. A method for the treatment of short gut syndrome, cul-de-sac syndrome, indigestible malabsorption syndrome and dumping syndrome, comprising:

administering an effective amount of glicentin to a subject suffering from one of said syndromes.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 69 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:1:

```
Arg  Ser  Leu  Gln  Asp  Thr  Glu  Glu  Lys  Ser  Arg  Ser  Phe  Ser  Ala  Ser
 1                  5                        10                       15

Gln  Ala  Asp  Pro  Leu  Ser  Asp  Pro  Asp  Gln  Met  Asn  Glu  Asp  Lys  Arg
                20                       25                       30

His  Ser  Gln  Gly  Thr  Phe  Thr  Ser  Asp  Tyr  Ser  Lys  Tyr  Leu  Asp  Ser
               35                       40                       45
```

-continued

```
Arg  Arg  Ala  Gln  Asp  Phe  Val  Gln  Trp  Leu  Met  Asn  Thr  Lys  Arg  Asn
     50                      55                      60

Arg  Asn  Asn  Ile  Ala
65
```

( 2 ) INFORMATION FOR SEQ ID NO:2:

( i ) SEQUENCE CHARACTERISTICS:
        ( A ) LENGTH: 70 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:2:

```
Met  Arg  Ser  Leu  Gln  Asp  Thr  Glu  Glu  Lys  Ser  Arg  Ser  Phe  Ser  Ala
1                   5                        10                     15

Ser  Gln  Ala  Asp  Pro  Leu  Ser  Asp  Pro  Asp  Gln  Met  Asn  Glu  Asp  Lys
               20                      25                          30

Arg  His  Ser  Gln  Gly  Thr  Phe  Thr  Ser  Asp  Tyr  Ser  Lys  Tyr  Leu  Asp
          35                      40                     45

Ser  Arg  Arg  Ala  Gln  Asp  Phe  Val  Gln  Trp  Leu  Met  Asn  Thr  Lys  Arg
     50                      55                      60

Asn  Arg  Asn  Asn  Ile  Ala
65                       70
```

( 2 ) INFORMATION FOR SEQ ID NO:3:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:3:

```
CGTTCCCTGC  AGGACACTGA  AGAAAAATCT  CGTTCTTTCT  CTGCTTCTCA  GGCTGACCCA      60

CTGTCGGATC  CAGACCAGAT  GAACGAAGAC  AAACGTCATT  CTCAGGGTAC  TTTCACTTCT     120

GACTACTCTA  AATACCTGGA  CTCTCGTCGA  GCTCAGGACT  TCGTTCAGTG  GCTGATGAAC     180

ACTAAACGTA  ACCGTAACAA  CATCGCC                                            207
```